(12) United States Patent
Lukens et al.

(10) Patent No.: US 10,605,727 B2
(45) Date of Patent: Mar. 31, 2020

(54) NONLINEAR INTERFEROMETER SYSTEMS AND METHODS

(71) Applicant: UT-Battelle, LLC, Oak Ridge, TN (US)

(72) Inventors: Joseph M. Lukens, Knoxville, TN (US); Nicholas A. Peters, Knoxville, TN (US); Raphael C. Pooser, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 389 days.

(21) Appl. No.: 15/582,178

(22) Filed: Apr. 28, 2017

(65) Prior Publication Data

US 2017/0315054 A1    Nov. 2, 2017

Related U.S. Application Data

(60) Provisional application No. 62/415,025, filed on Oct. 31, 2016, provisional application No. 62/329,230, filed on Apr. 29, 2016.

(51) Int. Cl.
| | |
|---|---|
| *G01N 21/45* | (2006.01) |
| *G01B 9/02* | (2006.01) |
| *H01S 3/10* | (2006.01) |
| *G01J 3/26* | (2006.01) |
| *G01C 19/64* | (2006.01) |

(52) U.S. Cl.
CPC ......... *G01N 21/45* (2013.01); *G01B 9/02003* (2013.01); *G01B 9/02007* (2013.01); *G01J 3/26* (2013.01); *H01S 3/10007* (2013.01); *H01S 3/10023* (2013.01); *H01S 3/10053* (2013.01); *G01B 2290/55* (2013.01); *G01C 19/64* (2013.01)

(58) Field of Classification Search
CPC ................ G01N 21/45; G01B 9/02003; G01B 9/02007; H01S 3/06787; H01S 3/10007; H01S 3/10053
See application file for complete search history.

(56) References Cited

U.S. PATENT DOCUMENTS 3,816,754 A * 6/1974 Hodgson ................. H01S 3/305
359/327
5,504,763 A * 4/1996 Bischel ................. H01S 3/2333
372/108

(Continued)

OTHER PUBLICATIONS

Donley et al., "Double-pass acousto-optic modulator system," *Rev. Sci. Instrum.*, 76:063112-1-063112-6 (2005).

(Continued)

*Primary Examiner* — Eric L Bolda
(74) *Attorney, Agent, or Firm* — Klarquist Sparkman, LLP

(57) ABSTRACT

Nonlinear interferometers include a nonlinear optical medium that is situated to produce a conjugate optical beam in response to a pump beam and a probe beam. The pump, probe, and conjugate beams propagate displaced from each other along a common optical path. One of the beams is selectively phase shifted, and the beams are then returned to the nonlinear medium, with the selectively phase shift beam phase shifted again. The nonlinear medium provides phase sensitive gain to at least one of the probe or conjugate beams, and the amplified beam is detected to provide an estimate of the phase shift.

35 Claims, 9 Drawing Sheets

(56) References Cited

U.S. PATENT DOCUMENTS

| | | | | |
|---|---|---|---|---|
| 6,078,597 | A * | 6/2000 | Feuer | G02F 1/3523 372/11 |
| 7,061,960 | B2 * | 6/2006 | Krupke | H01S 3/22 372/55 |
| 2006/0285197 | A1 * | 12/2006 | McKinstrie | H01S 3/06758 359/333 |
| 2016/0359569 | A1 | 12/2016 | Dailey et al. | |
| 2017/0214474 | A1 | 7/2017 | Dailey et al. | |

OTHER PUBLICATIONS

Fang et al., "Experimental implementation of a nonlinear beamsplitter based on a phase-sensitive parametric amplifier," *Appl. Phys. Lett.*, 108:131106-1-131106-4 (2016).

Hudelist et al., "Quantum metrology with parametric amplifier-based photon correlation interferometers," *Nature Commun.*, 5:1-6 (Jan. 2014).

Jing et al., "Realization of a nonlinear interferometer with parametric amplifiers," *Appl. Phys. Lett.*, 99:011110-1-011110-3 (2011).

Kong et al., "Experimental investigation of the visibility dependence in a nonlinear interferometer using parametric amplifiers," *Appl. Phys. Lett.*, 102:011130-1-011130-4 (2013).

Li et al., "Effect of input phase modulation to a phase-sensitive optical amplifier," *Opt. Express*, 24:19871-19880 (Aug. 2016).

Marino et al., "Effect of losses on the performance of an SU(1,1) interferometer," *Phys. Rev. A*, 86:023844-1-023844-8 (2012).

Neo et al., "Phase-sensitive amplification of light in a $\chi^{(3)}$ photonic chip using a dispersion engineered chalcogenide ridge waveguide," *Opt. Express*, 21:7926-7933 (Apr. 2013).

Z. Y. Ou, "Enhancement of the phase-measurement sensitivity beyond the standard quantum limit by a nonlinear interferometer," *Phys. Rev. A*, 85:023815-1-023815-7 (Feb. 2012).

Tong et al., "Low-noise optical amplification and signal processing in parametric devices," *Adv. Opt. Photon.*, 5:318-384 (Aug. 2013).

Wang et al., "Experimental implementation of phase locking in a nonlinear interferometer," *App. Phys. Lett.*, 107:121106-1-121106-5 (2015).

Xin et al., "The effect of losses on the quantum-noise cancellation in the SU(1,1) interferometer," *Appl. Phys. Lett.*, 109:051107-1-051107-4 (2016).

Yurke et al., "SU(2) and SU(1,1) interferometers," *Phys. Rev. A*, 33:4033-4054 (Jun. 1986).

Zhang et al., "Phase-sensitive amplification in silicon photonic crystal waveguides," *Opt. Lett.*, 39:363-366 (Jan. 2014).

International Preliminary Report on Patentability from International Application No. PCT/US2017/030200, dated Oct. 30, 2018, 10 pages.

Chekhova et al., "Nonlinear interferometers in quantum optics," *Advances in Optics and Photonics*, 8:104-155 (Mar. 2016).

Fu et al., "Phase-sensitive four-wave mixing interferometer," *Optics Letters*, 39:4427-4430 (Aug. 1, 2014).

Herzog et al., "Frustrated Two-Photon Creation via Interference," *Physical Review Letters*, 72:629-632 (Jan. 31, 1994).

International Search Report and Written Opinion from International Application No. PCT/US2017/030200, dated Jul. 31, 2017 13 pages.

Jing et al., "Realization of a nonlinear interferometer with parametric amplifiers," *Applied Physics Letters*, 99:011110-1-011110-3 (2011).

Culshaw et al., "Fiber-Optic Sensing: A Historical Perspective," *Journal of Lightwave Technology*, 26(9):1064-1078, (May 2008).

Giese et al., "Phase sensitivity of gain-unbalanced nonlinear interferometers," arXiv:1712.06226v2, pp. 1-11 (Nov. 2017) (also published as Giese et al., "Phase sensitivity of gain-unbalanced nonlinear interferometers," *Physical Review A*, 96, 053863 (2017)).

Lee et al, "Interferometric Fiber Optic Sensors," *Sensors*, 12:2467-2486 (2012).

Liu et al., "Quantum enhanced joint measurement of multiple non-commuting observables with SU(1,1) interferometer," arXiv:1712.01553v2, pp. 1-6 (Dec. 2017).

Lukens et al., "A Broadband Fiber-optic Nonlinear Interferometer," *Applied Physics Letters*, 113:091103-1-091103-5 (Aug. 2018).

Lukens et al., "A naturally stable Sagnac-Michelson nonlinear interferometer," accepted author manuscript, pp. 1-5 (Nov. 2016) (also published as Lukens et al., "A naturally stable Sagnac-Michelson nonlinear interferometer," *Optics Letters*, 41(23):5438-5441 (Oct. 2016)).

Manceau et al., "Detection loss tolerant supersensitive phase measurement with an SU(1,1) interferometer," arXiv:1705.02662v2, pp. 1-8 (Jun. 2017) (also published as Manceau et al., "Detection loss tolerant supersensitive phase measurement with an SU(1,1) interferometer," *Phys. Rev. Lett.*, 119(22):1-8, 223604 (2017)).

Plick, et al., "Coherent-light-boosted, sub-shot noise, quantum interferometry," *New Journal of Physics*, 12:1-9, 083014 (2010).

Slavík et al., "Processing of optical combs with fiber optic parametric amplifiers," *Optics Express*, 20(9):10059-10070 (Apr. 2012).

Tong et al., "Towards ultrasensitive optical links enabled by low-noise phase-sensitive amplifiers," *Nature Photonics*, 5:430-436 (Jun. 2011).

Tong et al., "Ultralow Noise, Broadband Phase-Sensitive Optical Amplifiers, and Their Applications," *IEEE Journal of Selected Topics in Quantum Electronics*, 18(2):1016-1032 (Mar./Apr. 2012).

\* cited by examiner

NONLINEAR INTERFEROMETER SYSTEMS AND METHODS

CROSS REFERENCE TO RELATED APPLICATIONS

This application claims the benefit of U.S. Provisional Application No. 62/329,230, filed Apr. 29, 2016, and U.S. Provisional Application No. 62/415,025, filed Oct. 31, 2016, which are incorporated herein by reference in their entireties.

ACKNOWLEDGMENT OF GOVERNMENT SUPPORT

This invention was made with government support under Contract No. DE-AC05-00OR22725 awarded by the U.S. Department of Energy. The government has certain rights in the invention.

FIELD

The disclosure pertains to nonlinear interferometers.

BACKGROUND

Interferometers have been used to investigate fundamental physical principles such as to determine the existence of gravitational waves and to disprove the existence of an electromagnetic ether. Due to the many applications of interferometers, the improvement of interferometers remains an active area of research. In many cases, interferometers divide an input beam into two portions, one of which is then subject to a phase change associated with a parameter under investigation. The two portions are then recombined, and the resulting interference detected. Phase change detection sensitivity is generally related to beam power (i.e., number of photons) and the quantum state. Coherent states are typically associated with phase uncertainties that are proportional to $\sqrt{N}$, wherein N is a number of photons used. Such phase uncertainties correspond to the shot noise limit. Further improvements in detection sensitivity can be made using so-called squeezed light.

Another approach to reducing phase uncertainty is to increase the magnitude of a detected interference signal using a nonlinear interferometer (NLI). In such an interferometer, passive beam splitters are replaced by nonlinear optical parametric amplifiers. Unfortunately, conventional nonlinear interferometers have been implemented as Mach-Zehnder interferometers, typically requiring active stabilization, and improved NLI configurations are needed.

SUMMARY

Parametric amplifier-based nonlinear interferometers are disclosed which typically include a single nonlinear element traversed twice. Consequently, a sensing field passes through a phase-shifting element twice and accumulates twice the phase shift obtained in single pass geometries. In one example, beams associated with the parametric amplifier propagate along nearly parallel paths, yielding intrinsic stability. With the exception of the phase-shifting element, all beams contact the same components, similar to a displaced-Sagnac interferometer. Such an arrangement can be referred to as a Sagnac-Michelson configuration as it exhibits advantages similar to both, such as increased stability due to substantially common path propagation.

In a representative example, nonlinear interferometers comprise a first beam source that produces a first beam at a first frequency and a second beam source that produces a second beam at a second frequency. An optical nonlinear medium receives the first beam and the second beam, and produces a third beam at a third frequency in response to the first beam and the second beam. A reflector is situated to receive the first beam, the second beam, and the third beam from the optical nonlinear medium and return the first beam, the second beam, and the third beam to the optical nonlinear medium so as to provide a phase-dependent amplification or deamplification to the second and third beams. In typical examples, a phase modulator is situated to receive one of the first, second, and third beams from the optical nonlinear medium, phase modulate the received beam, and direct the phase-modulated beam the reflector. In further examples, the phase modulator is situated to receive the phase modulated beam from the reflector and phase modulate the phase modulated beam. In one specific example, the nonlinear medium is a rubidium vapor cell. In further examples, a focusing element such as a lens is situated to focus the first beam and the second beam so as to overlap in the nonlinear medium, wherein the first beam and the second beam propagate along parallel, displaced axes to the focusing element. In additional examples, the reflector includes at least a first reflective surface situated to reflect at least the second beam and the third beam so that the reflected beams are returned to the nonlinear element along return axes that are displaced from respective axes of incidence to the reflector. In one specific example, the first beam is reflected along with the second and third beams. In one embodiment, the reflector is a right-angle prism. In a specific example, the second beam is produced by frequency shifting a portion of the first beam.

Example implementations can be based on $\chi^{(2)}$ or $\chi^{(3)}$ nonlinearities. Using $\chi^{(3)}$ nonlinearities, a first beam and a second beam are used to produce a third (conjugate) beam. If either the second or third beam is amplified, the other should also be amplified due to the fact that in the $\chi^{(3)}$ based four wave mixing, two photons from the first beam are converted to one photon in each of the second and third beams to conserve energy. In other examples, a single pump beam to generate two NLI beams.

In some embodiments, a first fiber coupler is situated to receive the first beam and the second beam and couple the first beam and the second beam into the nonlinear medium and a second fiber coupler is situated to receive the first beam, the second beam, and the third beam and direct at least one of the beams to a phase modulator. In typical examples, the second fiber coupler is situated to receive the phase-modulated beam from the phase modulator and direct the phase modulated beam to the optical nonlinear medium. According to some examples, the optical nonlinear medium is a highly nonlinear optical fiber and a photodetector is situated to receive the amplified third beam. According to other examples, the optical nonlinear medium is any nonlinear optical element including standard single mode fiber, and the photodetectors receive any combination of the amplified second or third beams. In other representative examples, the first beam is a pump beam and the second beam is a probe beam having a power less than that of the pump beam, and the probe beam is directed to the phase modulator.

Methods comprise directing first and second optical beams into nonlinear medium to produce a third optical beam and directing the first, second, and third optical beams along a common optical path. One of the second optical beam and third optical beam is phase modulated along the common optical path and the phase modulated beam and the remaining beams are directed along the common optical path back into the nonlinear medium so as to apply a phase sensitive amplification to both the second optical beam and the third optical beam. The amplified beam is detected so as to determine the phase modulation. In one example, the first and second optical beams produce the third optical beam by four wave mixing. In some embodiments, the nonlinear medium is a single mode optical fiber. In still further examples, the first, second, and third optical beams are directed so as to propagate displaced from the common axis.

The foregoing and other objects, features, and advantages of the disclosed technology will become more apparent from the following detailed description, which proceeds with reference to the accompanying figures.

DETAILED DESCRIPTION

Figure 1A:
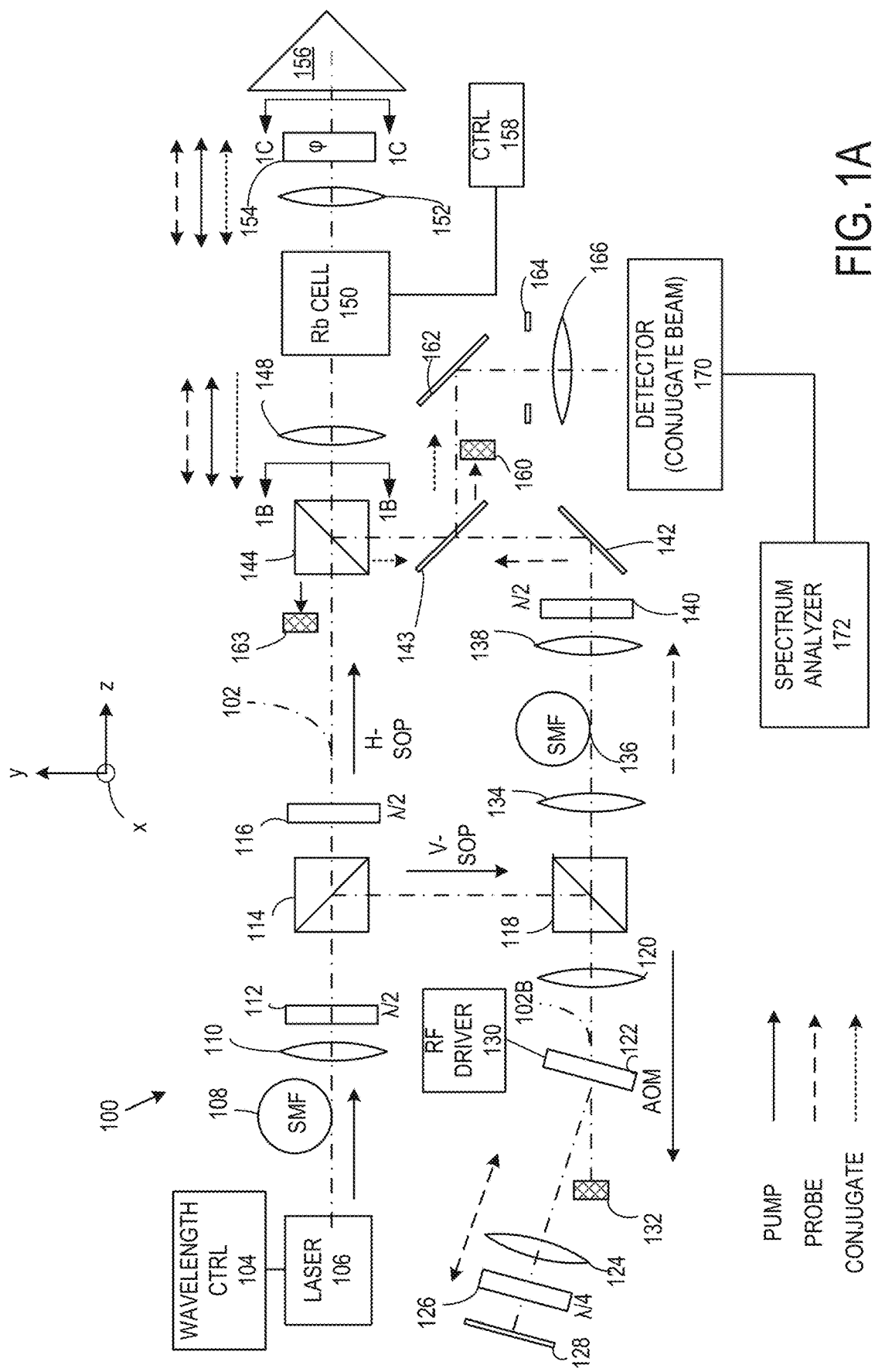
FIG. 1A illustrates a representative nonlinear interferometer (NLI).

As used in this application and in the claims, the singular forms "a," "an," and "the" include the plural forms unless the context clearly dictates otherwise. Additionally, the term "includes" means "comprises."

The described systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

Theories of operation, scientific principles, or other theoretical descriptions presented herein in reference to the apparatus or methods of this disclosure have been provided for the purposes of better understanding and are not intended to be limiting in scope. The apparatus and methods in the appended claims are not limited to those apparatus and methods which function in the manner described by such theories of operation.

As used herein, optical radiation refers to electromagnetic radiation at wavelengths of between about 100 nm and 10 µm, and typically between about 200 nm and 2 µm. Examples based on available laser diode sources and optical fibers generally are associated with wavelengths of between about 800 nm and 1700 nm. In some examples, propagating optical radiation is referred to as one or more beams having diameters, beam cross-sectional areas, and beam divergences that can depend on beam wavelength and the optical systems used for beam shaping. For convenience, optical radiation is referred to as light in some examples, and need not be at visible wavelengths.

For convenience, beams are described as propagating along one or more axes. Such axes generally are based on one or more line segments so that an axis can include a number of non-collinear segments as the axis is bent or folded or otherwise responsive to mirrors, prisms, lenses, and other optical elements. The term "lens" is used herein to refer to a single refractive optical element (a singlet) or a compound lens that includes one or more singlets, doublets, or other compound lenses. In some examples, beams are shaped or directed by refractive optical elements, but in other examples, reflective optical elements such as mirrors are used, or combinations of refractive and reflective elements are used. Such optical systems can be referred to as dioptric, catoptric, and catadioptric, respectively. Other types of refractive, reflective, diffractive, holographic and other optical elements can be used as may be convenient.

Optical components, devices, and beams are described as being situated along or propagating along an axis. In some examples, one or more components, beams, and or devices are displaced from the axis, and some beams propagate generally along an axis but beam propagation direction is varied with one or more lenses, mirrors, prisms, or other components. For example, a beam propagating parallel to an axis can be focused with a lens or mirror so as to propagate to a focus along a propagation direction that is not parallel to the axis. Beam focus can be on or off the axis, as is desired.

Optical beams are shown in some cases as having circular cross-sections, but beams of other shapes can be used, and beams propagating in a lowest order mode, or one or more higher order modes, or combinations of various modes can be used. Beam states of polarization (SOPs) are typically described as horizontal (H) or vertical (V) with respect to a selected coordinate axis, but elliptical SOPs, circular SOPs, and other linear SOPs can be used.

Nonlinear media of various kinds can be used including Rb vapor, crystalline or isotropic nonlinear materials having nonzero values of second or third order nonlinear polarizability. Examples include highly nonlinear fibers such as narrow-core fibers with silica cladding, typically having a small mode field diameter and a high doping so as to reduce effective beam area and increase nonlinear susceptibility. Alternatively, tapered fibers with air cladding can be used, which can be formed by heating and stretching, microstructured fibers having air or filled holes in a cladding. Holes can be filled with an inert gas or a liquid or other material. Regular arrays of holes can be provided to form highly nonlinear photonic crystal fibers. Non-silica fibers or other non-silica waveguides can be used, wherein the waveguides are based on one or more of lead silicates, chalcogenides, tellurite oxide, or bismuth oxide. Nonlinear waveguides can be defined in planar waveguides such as silica, polymer, or other materials that are situated on a planar or other substrate such as, for example, silicon, quartz, or other insulators or semiconductors. Highly nonlinear fibers (HNFs) are commercially available. In some examples, HNFs are germanium-doped silica fibers with low dispersion slopes and a small effective mode diameters.

Some nonlinear optical interactions are described below with reference to interaction of a pump beam and a probe beam to form a conjugate beam that is then phase stable with respect to the pump and probe beams. Typically pump beam power is relatively high, and this high pump beam power provides gain for a conjugate beam that is either generated by mixing of the pump and probe beams or amplified by the pump and probe beams. While it is typically convenient to direct a conjugate beam produced by the pump and probe beams to a phase modulator (such as provided by an optical sensor), one or more of the pump, probe, or conjugate beams can be similarly phase modulated. In some cases, beams are referred as pump, signal, and idler beams, and are generally associated with parametric amplification. In some cases, interacting beams are more simply noted as first, second, and third beams. The first beam, the second beam, and the third beam are generally associated with representative frequencies $v_1$, $v_2$, $v_3$, such that $v_1-v_2=v_3-v_1$ but other frequencies and combinations thereof can be used.

It will be appreciated that many materials have non-zero values of second and third order nonlinear coefficients, but in practical examples, materials having large values of $\chi^{(2)}$ or $\chi^{(3)}$ are preferred. Because the disclosed NLIs generally are arranged so that beams propagate to and from devices under test along a common path, phase stability requirements are less than for other arrangements such as Mach-Zehnder interferometers that can have long path differences. The beams generally propagate along the common path from the nonlinear material used to produce a conjugate or other beams to a reflector that returns the beams to the nonlinear materials along the common path.

The disclosed examples of NLIs are described with reference to four-wave mixing (FWM) in $^{85}$Rb vapor, but in other examples, three wave mixing is used. Parametric amplification can result from four wave mixing in a $\chi^{(3)}$ nonlinearity or three wave mixing in a $\chi^{(2)}$ nonlinearity. FWM is generally associated with interaction of at least two optical beams at different frequencies in a material having a third order nonlinearity to generate optical beams at one or more different frequencies, and other non-linear materials can be used as noted above, including materials that exhibit a second order nonlinearity or third order nonlinearity. Nonlinear materials based on third order nonlinearity tend to be convenient, as such materials can be isotropic, and alignment with nonlinear symmetry axes of second order materials is not needed. For example, silica-based fibers are generally centrosymmetric and do not generally exhibit $\chi^{(2)}$ nonlinearity but can provide, parametric amplification based on a third order nonlinearity $\chi^{(3)}$, using two pump frequencies, a signal frequency, and a conjugate frequency.

In one partially degenerate example, only a single pump frequency is used. Parametric gain bandwidth in fibers has a limited spectral range, and this spectral range is greater in fibers having low chromatic dispersion. In any of the nonlinear configurations discussed above, nonlinear beam interactions in the nonlinear material can produce phase-sensitive amplification, permitting improved signal to noise ratio in interferometry as discussed further below. So-called highly nonlinear fibers that are commercially available can be used. Nonlinear processes can require interaction of beams in specific states of polarization (SOPs), but SOP control and associated devices are omitted in some examples for convenient explanation.

In some examples, optical fibers or other waveguides are used. In some cases, fiber couplers are used to combine and divide optical beams. As used herein, a fiber coupler is a splitter or combiner that combines or splits with or without substantial wavelength sensitivity. Such devices can be lossy in splitting and combining as optical power is directed to unwanted fibers or other ports. As used herein, a fiber multiplexer refers to a device that is wavelength sensitive so as to provide more efficient splitting and combining Such devices are readily available, particularly for wavelengths associated with wavelength division multiplexed communication systems.

In some examples, optical parametric amplification is used and described with reference to a pump beam, an idler beam, and a signal beam having respective frequencies $v_p$, $v_i$, and $v_s$, wherein $v_p=v_i, +v_s$. Such parametric amplification is generally based on a second order optical nonlinearity.

In the examples below, phase dependent gain is provided using nonlinear optical interactions such as four wave mixing or three wave mixing. Such gain permits increased signal to noise ratios, and therefore increased phase detection sensitivity over conventional interferometers. The nonlinear medium produces beams that can have different interactions with a phase object of interest, and beam overlap in the nonlinear medium provide phase dependent gain. In this way, the nonlinear medium and the associated nonlinear processes serve as "nonlinear beam splitters" that can be used in various interferometers. However, in most examples, beams propagate along a common path to reflector, optical fiber, or other device that returns the beams back along the common path to the nonlinear medium, thus increasing NLI stability.

The disclosed approaches can be used to interrogate phase shift devices of various kinds, typically any optical sensor element that produces a phase shift. Examples include sensors based on optical phase changes produced in MEMS devices, electro-optic or acousto-optic devices, or in optical fibers or other media. Example sensors include fiber coils that are used to monitor acoustic signals, fiber optic gyroscopes, or other sensors that provide a phase change associated with measurement of a quantity of interest.

As described below, one port of the nonlinear beam splitter receives an optical beam (typically referred to as a probe beam), and amplifies the beam independent of input phase, stimulating production of a conjugate beam. In a second amplification (such as after phase modulation), the gain is phase-sensitive and, in principle, adds minimum noise allowed by quantum mechanics. As the phase-sensitive gain can be high relative to the added noise, the signal-to-noise ratio (SNR) can be improved. Thus, compared to a linear interferometer, interference fringe maxima are increased even though the same number of probe photons is input into the interferometer. In the high-gain limit, this leads to an SNR improvement of approximately twice the intensity gain. The examples below generally use a single nonlinear element traversed twice, much as a beam splitter in a linear Michelson interferometer. Consequently, the sensing beam passes through a phase-shifting element twice and accumulates double the phase compared to other approaches. In contrast to a conventional Michelson interferometer, the beams travel along near-parallel paths, yielding intrinsic stability. With the exception of the phase-shifting element, all fields typically contact with the same components, similar to a displaced-Sagnac interferometer.

FIG. 1A illustrates a representative NLI 100 that is shown as arranged along an axis 102, though beams may propagate generally parallel to but displaced from the axis 102. A laser 106 is situated to direct a pump beam at a pump frequency $v_{pump}$ (shown generally as an arrow using a solid line) along the axis 102. The laser 106 is coupled to a laser driver 104 that establishes laser power, wavelength, and other beam parameters. A laser is generally used to provide a pump beam due to the availability of relatively high power beams with narrow spectral bandwidths.

The pump beam is coupled to a single mode fiber (SMF) 108, which acts as spatial mode filter, and after propagation through the SMF 108, the pump beam is collimated with a lens 110 and directed to a half-wave retarder 112 that is rotatable to select a polarization direction of the pump beam. The pump beam is then coupled to a polarizing beam splitter (PBS) 114 that directs a first state of polarization (SOP) portion of the pump beam to a half-wave retarder 116 and a second SOP portion to a PBS 118. Typically, the PBS 114 transmits a horizontal (H) SOP (in the plane of FIG. 1) and reflects a vertical (V) SOP (perpendicular to the plane of FIG. 1).

The PBS 118 reflects the V-polarized portion of the pump beam to a lens 120 that directs the beam to an acousto-optic modulator (AOM) 122 that produces a diffracted beam that is directed to a lens 124, a quarter wave retarder 126, and a reflector 128. The reflected, diffracted beam is returned to the AOM 122 and diffracted so as to propagate along an axis portion 102B. The reflected, twice diffracted beam is referred to as a probe beam, and is frequency offset by twice a drive frequency applied to the AOM 122 by an RF source 130 and propagates at a probe beam frequency $v_{probe} = v_{pump} - 2 v_{AOM}$, wherein $v_{AOM}$ is an acousto-optic modulation frequency of the AOM 122. In one example, the acousto-optical modulation frequency is 1.52 GHz, and a beam frequency shift is 3.04 GHz. One or more of the pump and probe beams can be amplitude modulated as well to simplify detection of fringe signals. In one example, the probe beam is amplitude modulated at 750 kHz. Undiffracted pump beam portions can be captured by a beam dump 132 or otherwise blocked. Power division between the pump beam as transmitted by the PBS 114 and the probe beam can be controlled based on a rotation of the half wavelength retarder 112.

The probe beam is further coupled by a lens 134 to a single mode fiber (SMF) 136 and then by a lens 138 through a half wave retarder 140 to a reflector 142 that directs the probe beam to a PBS 144. A reflector 143 is situated between the reflector 142 and the PBS 144 but is situated so that the probe beam is directed around the reflector 143 as discussed below.

Figure 1B:
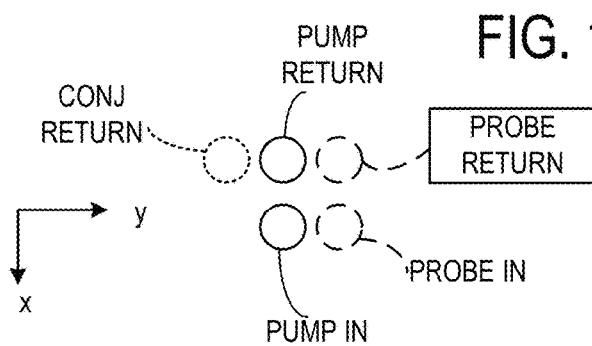
FIGS. 1B-1C illustrate representative beam displacements in the nonlinear interferometer of FIG. 1A.
Figure 1D:
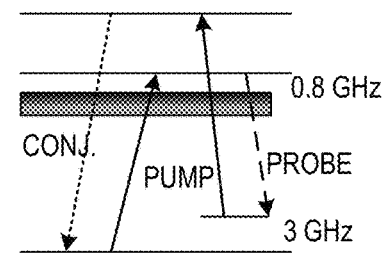
FIG. 1D illustrates energy levels in Rubidium vapor used as a nonlinear material in the NLI of FIG. 1A.
Figure 1C:
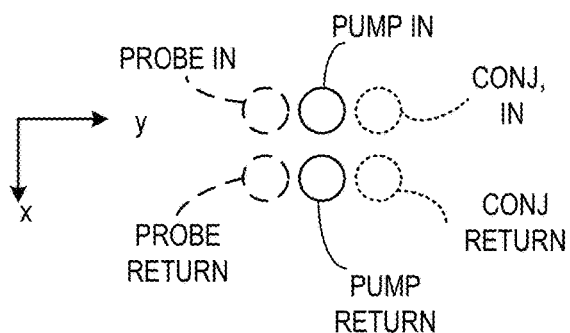

The probe beam (V-SOP) and the pump beam (H-SOP) propagate from the PBS 144 along the axis 102 to a lens 148 that focuses the probe and pump beams so as to overlap in a rubidium vapor cell 150, generating a conjugate beam by four wave mixing. The pump, probe, and conjugate beams propagate along the axis 102 but are offset as shown in FIGS. 1B-1C. The Rb cell temperature is controlled with a thermal controller 158, and suitable heaters and temperature sensors can be provided. Pump, probe, and conjugate beams then are collimated by a lens 152, and one or more of the beams is directed through a phase object 154. The pump, probe, and conjugate beams then are returned by a prism 156 to the lens 152, focused into the Rb cell 150, and the conjugate beam is subject to phase sensitive amplification based on the pump and probe beams in the Rb cell 150. The prism 156 is shown as a right angle prism having surfaces at a right angle in the plane of FIG. 1A for convenient illustration, but is typically oriented so that the prism angle is defined in a plane perpendicular to the plane of FIG. 1A so as to be associated with beam positions shown in FIGS. 1B-1C as discussed below.

The amplified conjugate beam, the probe beam, and the pump beam then are directed by the lens 148 to the PBS 144; the pump beam is sent to a beam dump 163 while the conjugate beam is directed by reflectors 143 and 162 through aperture 164 to a lens 166 and a detector 170. The detector is coupled to an electrical spectrum analyzer 172, and signal portions at frequencies corresponding to the amplitude modulation of the probe beam discussed above can be associated with phase modulation by the phase object 154.

FIGS. 1B and 1C illustrate beam cross-sections at sections BB and CC in FIG. 1A. While the pump, probe, and conjugate beams generally propagate as parallel beams, they are offset and are focused so as to overlap in the Rb cell 150 to provide nonlinear mixing for generation and phase sensitive amplification of a conjugate beam. Either the probe, conjugate, or the pump beam could be selected for interrogation of the phase object 154 as each of the beams is displaced from the others along the axis 102, and are focused to overlap in the nonlinear medium (the Rb cell 150). Beam positions in FIG. 1B and FIG. 1C are generally flipped due to focusing by the lenses and reflection by the prism 156.

Spatial mode filtering can boost fringe contrast, providing visibilities up to (99.93±0.01)% especially if the measured beam is modulated so as to be at a frequency displaced from lower-frequency background noise. An aperture 164 can be adjusted to provide spatial mode filtering. In the example of FIG. 1A, a relatively powerful pump field and a relatively weak probe seed beam are focused into a parametric amplifier (the Rb cell 150) to generate the conjugate beam. As shown, the probe beam experiences a phase shift before all three beams reflect back into the amplifier for phase sensitive mixing. Finally, the conjugate field is detected, and its intensity is related to the phase shift. Alternative detection schemes are possible, such as summing the probe and conjugate outputs or homodyne/heterodyne detection with a local oscillator.

The phase sensitive parametric amplification used in FIG. 1A can be implemented in fiber optic systems and in on-chip photonic waveguides. Various beam sources can be used to provide one or more of the necessary beams. A narrowlinewidth Ti:Sapphire laser at ~795 nm is suitable, and can be coupled into optical fiber for mode clean up before splitting at the PBS 114. In other examples, other sources such as diode lasers, gas lasers, other solid state lasers can be used. In some cases, one or more of the pump, probe, and conjugate beams are spatially filtered using a suitable aperture and focusing optics, or by propagation in an optical fiber such as a single mode optical fiber.

The configuration of FIG. 1A has been demonstrated as a system in which a 50 cm focal-length lens focused pump and probe beams with a crossing angle of 8 mrad into a 12.7 mm long $^{85}$Rb vapor cell heated to ~120° C. The pump beam (and consequently the probe beam) wavelength is scanned and locked to maximize FWM gain as shown in an energy level diagram of FIG. 1D. The pump, probe, and newly generated conjugate are reimaged into the Rb cell in a 4 f-system, with the probe phase-shifted by a rotatable glass slide. All three beams are vertically displaced with a right-angle prism retroreflector. Such displacement ensures that the return fields propagate in different spatial modes through the Rb vapor, suppressing unwanted nonlinear interactions between forward- and back-propagating fields and enabling easy separation of the output fields from the inputs. Other types of prisms and reflectors can be used such as corner cubes, and reflective surfaces can be defined by one or more substrates to reduce reflector bulk such as air spaced surfaces that have arrangements similar to prism surfaces.

Figure 2A:
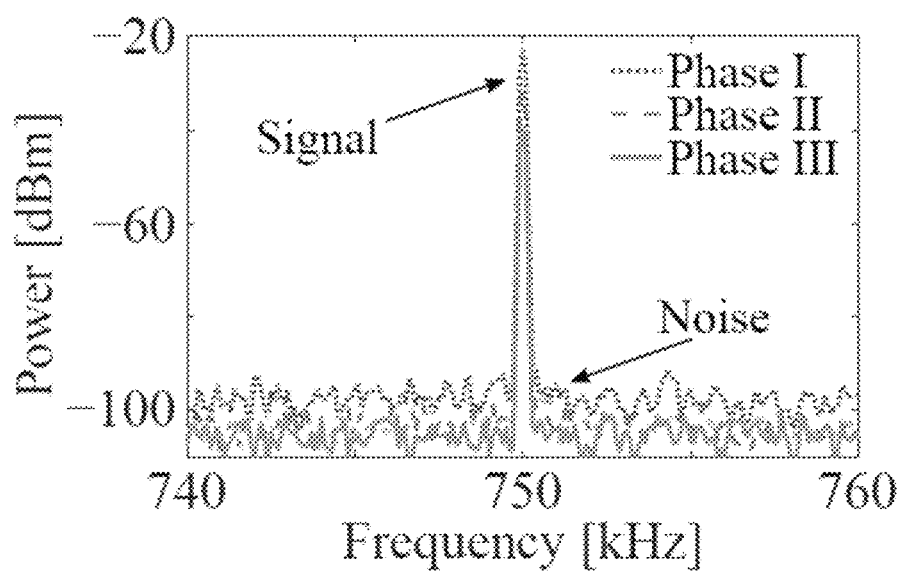
FIG. 2A illustrates signal power as a function of phase for the NLI of FIG. 1A at a selected modulation frequency.
Figure 2B:
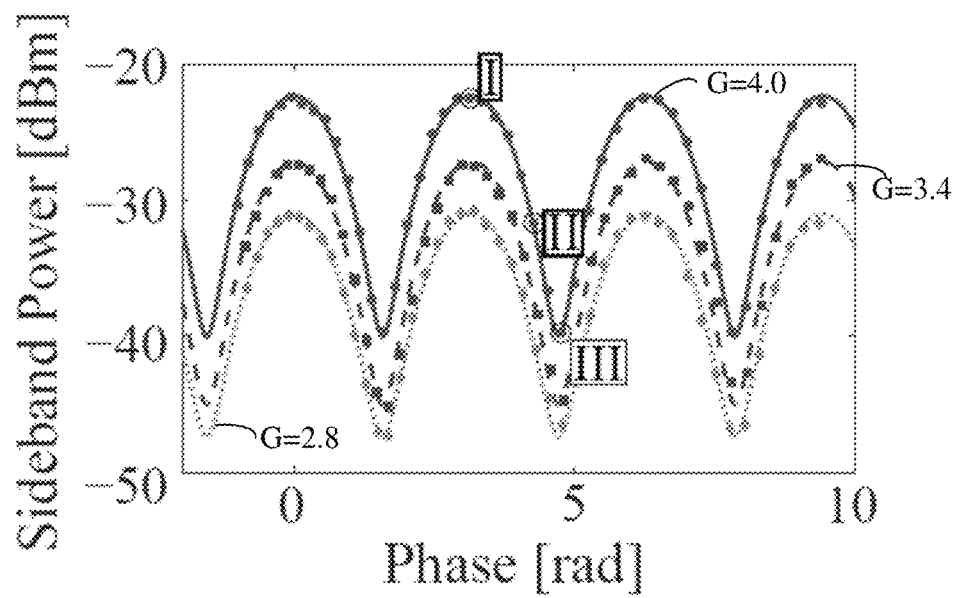
FIG. 2B illustrates interference fringes obtained with the NLI of FIG. 1A at different gain settings.
Figure 3:
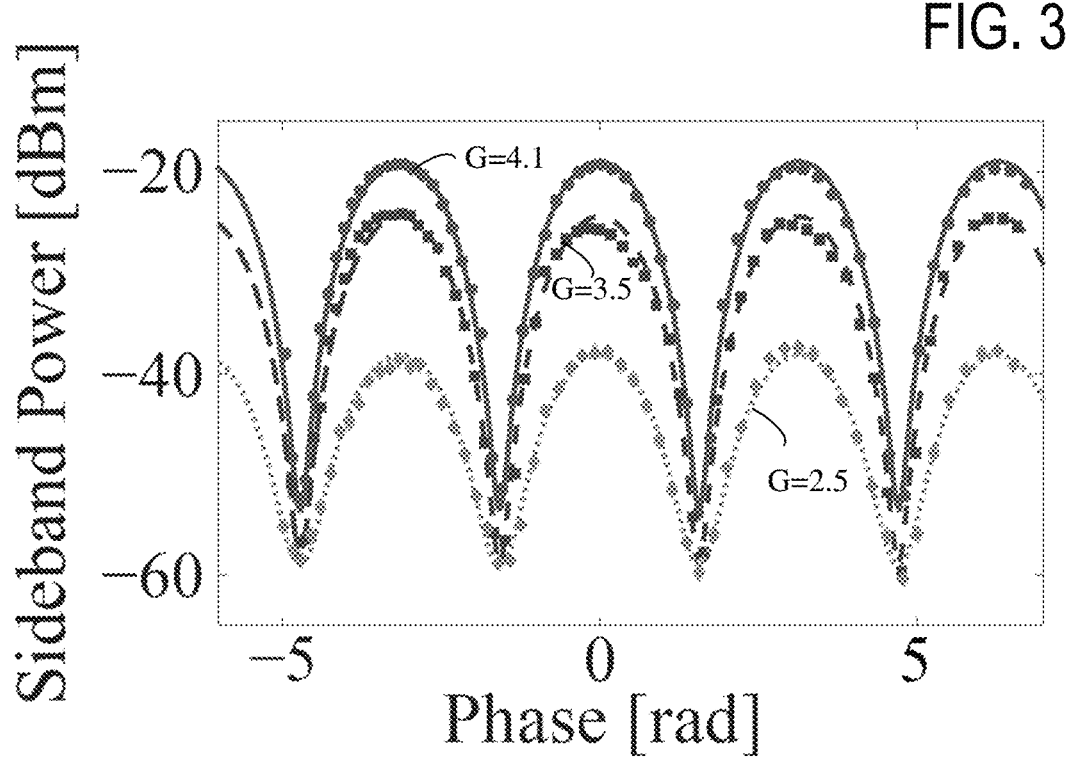
FIG. 3 illustrates interference fringes obtained with the NLI of FIG. 1A at different gain settings.

For the example implementation, FIG. 2A shows power at the 750-kHz modulation frequency for three different phase settings, illustrating the large signal to noise ratio available. FIG. 2B shows signal power as a function of phase shift at phase sensitive gains of 2.8, 3.4, and 4.0. FIG. 3 illustrates interference fringes obtained with the NLI of FIG. 1A with aperture 164 closed to a smaller opening, at gain settings (G=2.5, 3.5, 4.1).

Figure 4:
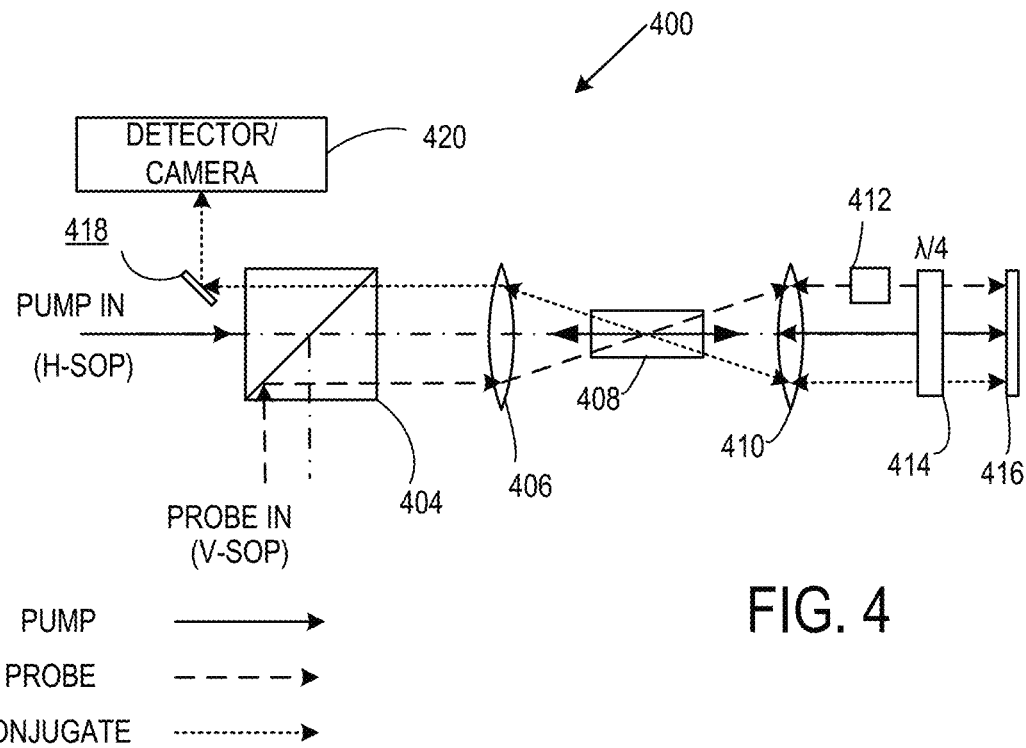
FIG. 4 illustrates another representative nonlinear interferometer.

With reference to FIG. 4, a representative NLI 400 includes a PBS 404 which receives a pump beam in a horizontal SOP and a probe beam in a vertical SOP. The combined beams are directed to a lens 406 that focuses the pump beam and the probe beam in a nonlinear medium 408 to overlap so as to produce an additional beam, referred to generally as a conjugate beam at a frequency based on a sum or difference or other combination of the frequencies of the pump beam and the probe beam through a nonlinear optical interaction such as four wave mixing. The pump, probe, and conjugate beams are collimated by a lens 410 and coupled through a quarter wave retarder 414 and a reflector 416. A selected beam (one of the pump, probe, or conjugate beams) is directed through a phase modulator 412 as well.

The pump, probe, and conjugate beams are returned to the nonlinear medium 408 by the quarter wave retarder 414 and the lens 410, with the selected one of the pump, probe, or conjugate beam traversing the phase modulator 412 again. The nonlinear medium provides phase sensitive amplification to the conjugate beam that is coupled by the lens 406, the PBS 404, and a reflector 418 to a camera or other detector 420.

Figure 5:
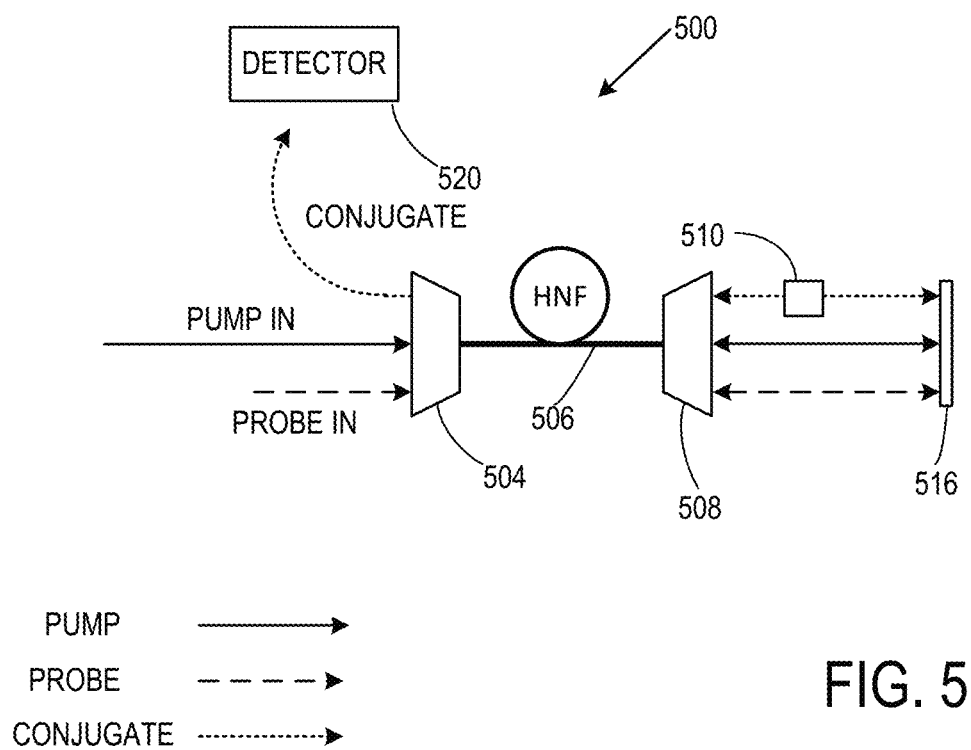
FIG. 5 illustrates a representative nonlinear interferometer that includes a nonlinear optical fiber.

Referring to FIG. 5, an NLI 500 is coupled to receive pump and probe beams that are provided to a fiber multiplexer 504 that delivers the combined beams to a single mode fiber or other fiber such as a highly nonlinear fiber (HNF) 506 that produces a conjugate beam based on a nonlinear interaction of the pump and probe beams. A demultiplexer 508 receives pump, probe, and conjugate beams and outputs these beams separately. As shown in FIG. 5, the conjugate beam is directed through a phase modulator 510, and the pump, probe, and conjugate beams are all directed to a reflector 516 and then back to the multiplexer 508. The returned beams are coupled into the HNF fiber 506 for phase sensitive amplification, and the amplified conjugate beam is coupled by the multiplexer 504 to a detector 520. The multiplexers 504, 508 typically include fiber inputs and outputs such as single mode fibers or polarization maintaining fibers. In the example of FIG. 5, multiple beams co-propagate in the HNF 506, and spatial beam separation is not needed.

Figure 11:
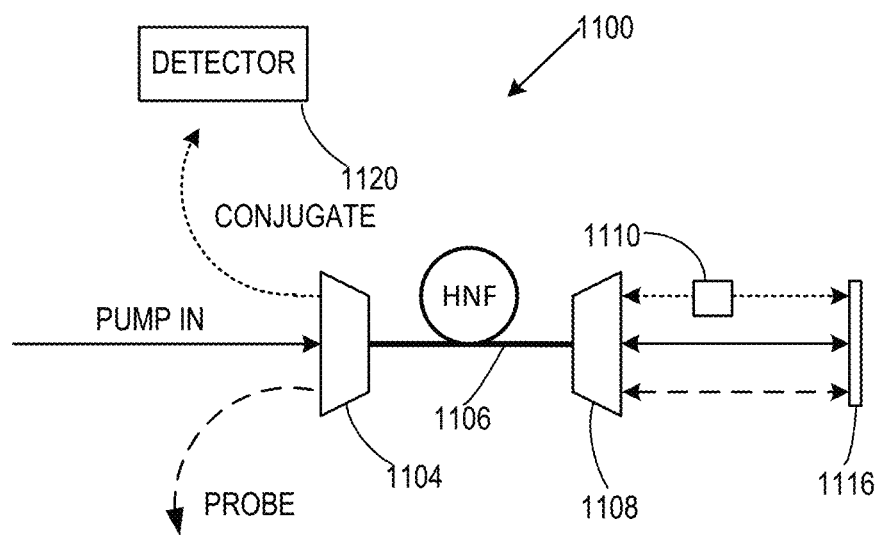
FIG. 11 illustrates a representative nonlinear interferometer that includes a nonlinear optical fiber.

In another example shown in FIG. 11, a $\chi^{(3)}$ interaction is used and single input (pump) beam is used to produce a probe beam and a conjugate beam. An NLI 1100 is coupled to receive a pump beam that is provided to a fiber multiplexer 1104 that delivers the pump beam to a single mode fiber or other fiber such as a highly nonlinear fiber (HNF) 1106 that produces two beams referred to herein as a conjugate beam and a probe beam based on a nonlinear interaction of the pump beam with the HNF 1106. A demultiplexer 1108 receives pump, probe, and conjugate beams and outputs these beams separately. As shown in FIG. 11, the conjugate beam is directed through a phase modulator 1110, and the pump, probe, and conjugate beams are all directed to a reflector 1116 and then back to the multiplexer 1108. The returned beams are coupled into the HNF fiber 1106 for phase sensitive amplification, and the amplified conjugate beam (and/or the probe beam) is coupled by the multiplexer 1104 to a detector 1120. The multiplexers 1104, 1108 typically include fiber inputs and outputs such as single mode fibers or polarization maintaining fibers.

Figure 6:
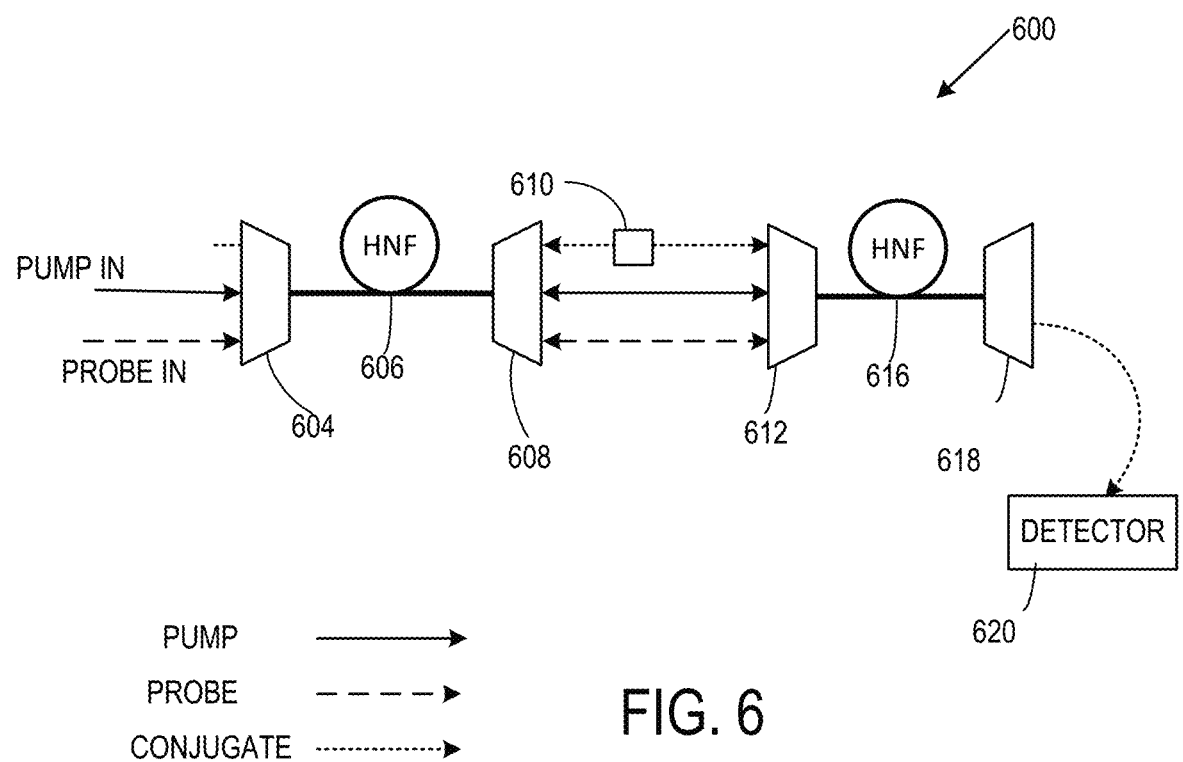
FIG. 6 illustrates a representative nonlinear interferometer that includes two nonlinear optical fibers.

Another representative NLI 600 is illustrated in FIG. 6. Pump and probe beams are directed to a wavelength multiplexer 604 that couples the beams to a highly nonlinear fiber 606 to produce a conjugate beam. While couplers can be used, wavelength multiplexers are generally preferred as they typically are less lossy. The pump, probe, and conjugate beams are wavelength demultiplexed 608 so that the beams propagate separately to a wavelength multiplexer 612, with one of the beams (shown as the conjugate beam) selected to be transmitted by a phase modulator 610. The pump, probe, and conjugate beams are coupled to an HNL fiber 616 for phase sensitive amplification, and the beams are split after phase sensitive amplification at a wavelength demultiplexer 618. The selected beam (the conjugate beam as shown) is coupled to a detector 620. While the configuration of FIG. 6 can be implemented with waveguide devices such as optical fibers, two nonlinear devices are used, one to generate the conjugate beam, and a second to provide phase sensitive amplification. Multiplexers are generally preferred to couplers in the configuration of FIG. 6, but couplers can be used as well.

Figure 7:
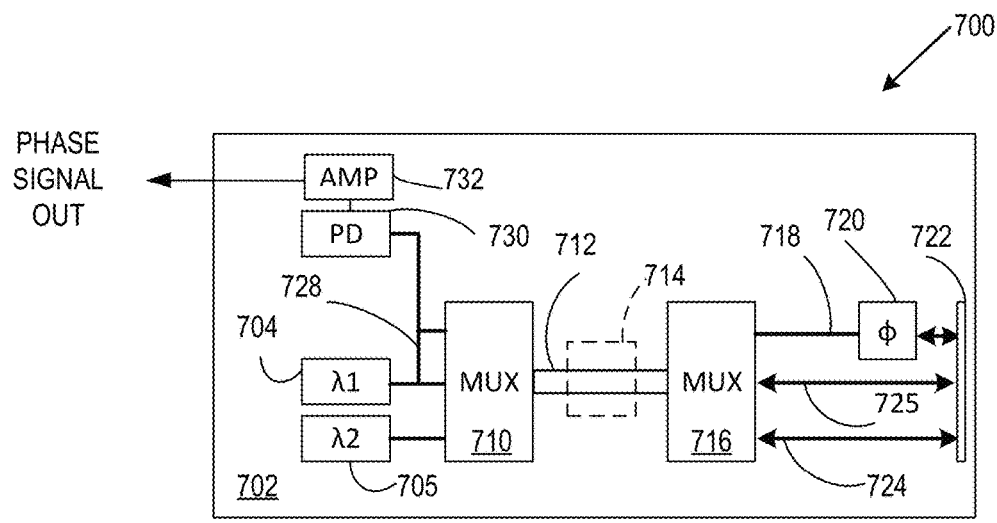
FIG. 7 illustrates an integrated nonlinear interferometer with an on-board phase shift element.

FIG. 7 illustrates an NLI 700 formed on a substrate 702. Laser diodes 704, 705 are coupled to provide pump and probe beams to a wavelength sensitive waveguide multiplexer 710 that couples the beams to a nonlinear fiber 712, a nonlinear waveguide, or other nonlinear medium such as Rb vapor in a cell 714. The pump beam and probe beam interact to produce a conjugate beam, and these beams are coupled to a multiplexer 716. A first output fiber 718 couples one of the beams (such as the probe beam) to a phase modulator 720 and a reflector 722 that return a modulated beam to the multiplexer 716. The remaining beams are coupled to respective fibers 724, 725 and returned to the multiplexer 716 as well. The recombined beams are directed back to the nonlinear fiber 712 for phase sensitive amplification, and the multiplexer 710 directs a selected beam such as the probe beam to a photodiode 730 or other photodetector that is typically coupled to a transimpedance or other amplifier 732. FIG. 7 also shows a waveguide 728 that is coupled to direct a portion of one of the pump or probe beams to the photodiode 730 as well to provide a local oscillator beam for coherent detection.

Figure 8:
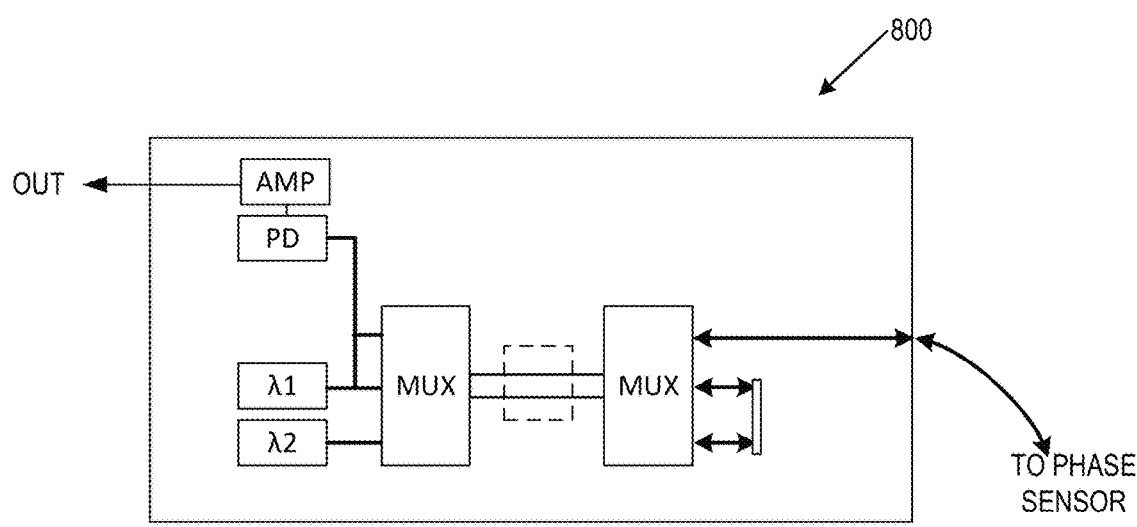
FIG. 8 illustrates an integrated nonlinear interferometer configured to be coupled to a remote phase sensing element.

FIG. 8 illustrates an NLI 800 similar to that of FIG. 7, but includes an output that couples a probe beam (or other beam) to and from a phase-based sensor such as an optical hydrophone, a fiber optic gyroscope, or other sensor.

Figure 9:
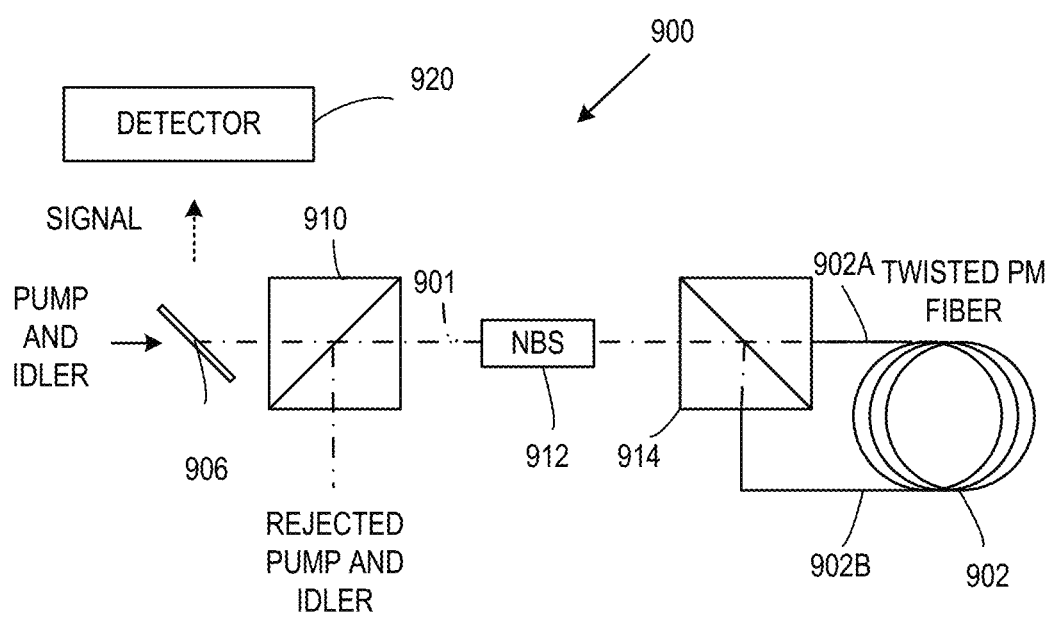
FIG. 9 is an NLI coupled to determine a phase shift based on the Sagnac effect.

FIG. 9 illustrates a NLI that is coupled to receive a Sagnac phase shift produced in a twisted polarization maintaining (PM) fiber 902, such as in a fiber optical gyroscope. Pump and idler beams at respective frequencies are directed through a dichroic mirror 906 along an axis 901 to a PBS 910. A nonlinear medium 912 receives the pump and idler beams and produces a signal beam at a signal beam frequency. The beams are coupled to the twisted PM fiber 902 at surfaces 902A, 902B by a PBS 914 based on beam SOPs to produce counter-propagating beams. The twist of the twisted PM fiber 902 is selected so that the pump, idler, and signal beams are returned to the PBS 914 in polarizations opposite to the launch polarizations. For example, horizontal linear polarizations at surface 902A become vertical at surface 902B after propagation through the twisted PM fiber 902. A phase shift φ between the beams is proportional to an angular rotation rate ω of the twisted PM fiber 902, a number of fiber loops N, and a loop area, i.e. φ~NAω. The beams are returned to the nonlinear medium 912 and the PBS 910. The pump and idler beams can be in SOPs so as to be reflected by the PBS 910. In addition, the pump and idler beams are transmitted by the dichroic mirror 906 while the amplified signal beam is reflected by the dichroic mirror 906 to a detector 920.

Figure 10:
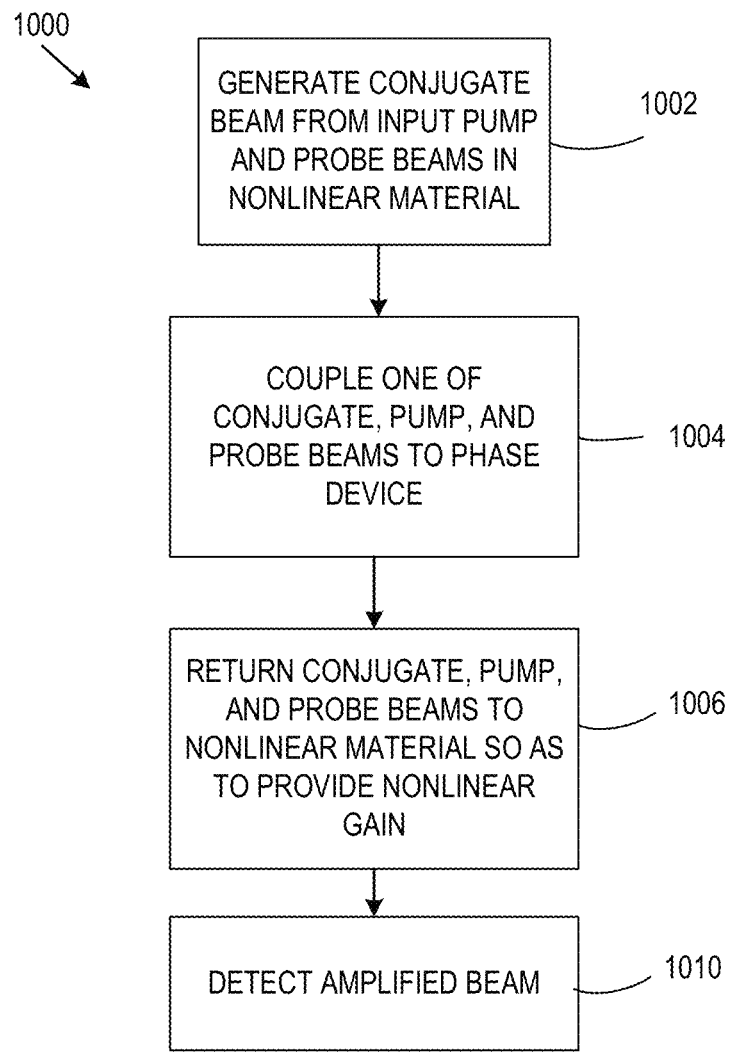
FIG. 10 illustrates representative method of performing nonlinear interferometry using input beams propagating toward a sensor element along a common path, and returning to a nonlinear material along the common path for phase sensitive amplification of at least one input beam.

Referring to FIG. 10, a representative method 1000 includes generating a conjugate beam from a pump beam and a probe beam in an optical nonlinear material at 1002. In some examples, the beams can be referred to as pump, idler, and signal beams based on conventional terminology for optical parametric amplification. At 1004, a selected beam is coupled to a phase shift device (such as an optical sensor) along a common optical path with the other beams. At 1006, the beams are returned to the nonlinear material along the common path, with the selected beam subject to the phase shift a second time. The beams interact in the nonlinear material at 1006 to provide phase dependent gain, and an amplified beam is detected at 1010. Typically, beams propagate to a sensor phase shift element along a common path but displaced from each other and are returned to the nonlinear material along the common path to improve stability. A focusing element (such as lens or mirror) is used to focus and overlap beams in the nonlinear material.

In view of the many possible embodiments to which the principles of the disclosed technology may be applied, it should be recognized that the illustrated embodiments are only preferred examples and should not be taken as limiting the scope of the disclosure. We claim as our invention all that comes within the scope and spirit of the appended claims.

We claim:

1. A nonlinear interferometer, comprising:
a first beam source that produces a first beam at a first frequency;
a second beam source that produces a second beam at a second frequency;
an optical nonlinear medium that receives the first beam and the second beam, and produces a third beam at a third frequency in response to the first beam and the second beam;
a reflector situated to receive the first beam, the second beam, and the third beam from the optical nonlinear medium and return the first beam, the second beam, and the third beam to the optical nonlinear medium so as to provide a phase-dependent amplification to one or more of the first, second, or third beams; and
a phase modulator situated to receive at least one of the first, second, and third beams from the optical nonlinear medium, phase modulate the received beam, direct the phase-modulated beam to the reflector, receive the phase modulated beam from the reflector, and phase modulate the received phased modulated beam.

2. The nonlinear interferometer of claim 1, wherein the nonlinear medium is a rubidium vapor cell.

3. The nonlinear interferometer of claim 2, further comprising a focusing element situated to focus the first beam and the second beam so as to overlap in the nonlinear medium, wherein the first beam and the second beam propagate along parallel, displaced axes to the focusing element.

4. The nonlinear interferometer of claim 3, wherein the focusing element is a lens.

5. A nonlinear interferometer, comprising:
a first beam source that produces a first beam at a first frequency;
a second beam source that produces a second beam at a second frequency;
an optical nonlinear medium that receives the first beam and the second beam, and produces a third beam at a third frequency in response to the first beam and the second beam; and
a reflector situated to receive the first beam, the second beam, and the third beam from the optical nonlinear medium and return the first beam, the second beam, and the third beam to the optical nonlinear medium so as to provide a phase-dependent amplification to one or more of the first, second, or third beams, wherein the reflector includes at least a first reflective surface and a second reflective surface situated to reflect at least one of the first beam, second beam, and the third beam so that the reflected beam is returned to the nonlinear element along a return axis that is displaced from an axis of incidence to the reflector.

6. The nonlinear interferometer of claim 5, wherein the reflector is a right-angle prism or a corner cube.

7. The nonlinear interferometer of claim 1, wherein the second beam is produced by frequency shifting a portion of the first beam.

8. The nonlinear interferometer of claim 1, further comprising a first fiber coupler situated to receive the first beam and the second beam and couple the first beam and the second beam into the nonlinear medium.

9. The nonlinear interferometer of claim 8, further comprising a second fiber coupler situated to receive the first beam, the second beam, and the third beam and direct at least one of the beams to the phase modulator.

10. The nonlinear interferometer of claim 9, wherein the second fiber coupler is situated to receive the phase-modulated beam from the phase modulator and direct the phase modulated beam to the optical nonlinear medium.

11. The nonlinear interferometer of claim 10, wherein the optical nonlinear medium is a highly nonlinear optical fiber.

12. The nonlinear interferometer of claim 1, further comprising a photodetector situated to receive the amplified third beam.

13. The nonlinear interferometer of claim 1, wherein the first beam is a pump beam and the second beam is a probe beam having a power less than that of the pump beam, and the probe beam is directed to the phase modulator.

14. The nonlinear interferometer of claim 1, further comprising a photodetector situated to receive at least a portion of the third beam so as to detect the phase modulation applied by the phase modulator.

15. The nonlinear interferometer of claim 1, further comprising a first fiber wavelength multiplexer situated to receive the first beam and the second beam and couple the first beam and the second beam into the nonlinear medium.

16. The nonlinear interferometer of claim 15, further comprising a second fiber wavelength multiplexer situated to receive the first beam, the second beam, and the third beam and direct at least one of the beams to the phase modulator.

17. The nonlinear interferometer of claim 16, wherein the second fiber wavelength multiplexer is situated to receive the phase-modulated beam from the phase modulator and direct the phase modulated beam to the optical nonlinear medium.

18. The nonlinear interferometer of claim 17, wherein the optical nonlinear medium is a highly nonlinear optical fiber.

19. A method, comprising:
directing first and second optical beams into a nonlinear medium to produce a third optical beam;
directing the first, second, and third optical beams along a common optical path;
phase modulating one of the second optical beam and third optical beam along the common optical path;
directing the phase modulated beam and the remaining beams along the common optical path into the nonlinear medium to apply a phase sensitive amplification to at least one of the second optical beam and the third optical beam; and
detecting the amplified beam to determine the phase modulation.

20. The method of claim 19, wherein the first and second optical beams produce the third optical beam by four wave mixing or three wave mixing.

21. The method of claim 19, wherein the nonlinear medium is a single mode optical fiber.

22. A nonlinear interferometer, comprising:
a first beam source that produces a first beam at a first frequency;
an optical nonlinear medium that receives the first beam and produces a second beam at a second frequency and a third beam at a third frequency in response to the first beam; and
a reflector situated to receive the first beam, the second beam, and the third beam from the optical nonlinear medium and return the first beam, the second beam, and the third beam to the optical nonlinear medium so as to provide a phase-dependent amplification to one or more of the first beam, the second beam, or the third beam.

23. The nonlinear interferometer of claim 22, further comprising a phase modulator situated to receive one of the first, second, and third beams from the optical nonlinear medium, phase modulate the received beam, and direct the phase-modulated beam to the reflector.

24. The nonlinear interferometer of claim 23, wherein the phase modulator is situated to receive the phase modulated beam from the reflector and phase modulate the phase modulated beam.

25. The nonlinear interferometer of claim 24, wherein the reflector includes at least a first reflective surface and a second reflective surface situated to reflect at least one of the first beam, second beam, and the third beam so that the reflected beam is returned to the nonlinear element along a return axis that is displaced from an axis of incidence to the reflector.

26. The nonlinear interferometer of claim 25, wherein the reflector is a right-angle prism or a corner cube.

27. The nonlinear interferometer of claim 22, wherein the second beam is produced by frequency shifting a portion of the first beam.

28. The nonlinear interferometer of claim 22, further comprising a first fiber coupler situated to receive the first beam and couple the first beam into the nonlinear medium.

29. The nonlinear interferometer of claim 28, further comprising a second fiber coupler situated to receive the first beam, the second beam, and the third beam and direct at least one of the beams to a phase modulator.

30. The nonlinear interferometer of claim 22, wherein the optical nonlinear medium is a highly nonlinear optical fiber.

31. The nonlinear interferometer of claim 22, further comprising a photodetector situated to receive the amplified third beam.

32. The nonlinear interferometer of claim 22, further comprising a first fiber wavelength multiplexer situated to receive the first beam and couple the first beam into the nonlinear medium.

33. The nonlinear interferometer of claim 32, further comprising a second fiber wavelength multiplexer situated to receive the first beam, the second beam, and the third beam and direct at least one of the beams to a phase modulator.

34. The nonlinear interferometer of claim 33, wherein the second fiber wavelength multiplexer is situated to receive the phase-modulated beam from the phase modulator and direct the phase modulated beam to the optical nonlinear medium.

35. The nonlinear interferometer of claim 5, wherein the nonlinear medium is a rubidium vapor cell.

* * * * *